United States Patent [19]

Ernerot

[11] 4,236,633

[45] Dec. 2, 1980

[54] PROCESS FOR STORAGE

[75] Inventor: Lennart S. Ernerot, Södertälje, Sweden

[73] Assignee: Astra Läkemedel Aktiebolag, Södertälje, Sweden

[21] Appl. No.: 936,772

[22] Filed: Aug. 25, 1978

[30] Foreign Application Priority Data

Sep. 6, 1977 [SE] Sweden .................................. 7709970

[51] Int. Cl.³ .............................................. B65D 81/24
[52] U.S. Cl. .................................. 206/213.1; 206/524.4
[58] Field of Search ............... 206/524.8, 524.2, 524.4, 206/484.2, 213.1, 219

[56] References Cited

U.S. PATENT DOCUMENTS

| | | | |
|---|---|---|---|
| 1,081,592 | 12/1913 | Ehrlich | 206/524.4 |
| 3,369,859 | 2/1968 | Cornelius | 206/213.1 |
| 3,815,315 | 6/1974 | Glick | 206/524.8 |
| 4,089,415 | 5/1978 | Laib | 206/524.2 X |

*Primary Examiner*—Herbert F. Ross
*Attorney, Agent, or Firm*—Brumbaugh, Graves, Donohue & Raymond

[57] ABSTRACT

The present invention relates to a process for preventing decomposition by oxidation of substances sensitive to oxidation, which substances are present in pharmaceutically active preparations in the form of solutions. The preparations present in ampoules, disposable syringes, vials and the like are thereby enclosed in an outer package made of oxygen impervious material, into which outer package hydrogen and a catalyst, capable of catalyzing the reaction of hydrogen and oxygen to water, is introduced, and such a package.

11 Claims, No Drawings

PROCESS FOR STORAGE

The present invention relates to a process for preventing oxidation decomposition of substances sensitive to oxidation in pharmaceutically active preparations in the form of solutions, and a package for preventing such oxidation decomposition.

The object of the present invention is to obtain a possibility of storing for a long time of pharmaceutically active preparations in the form of solutions, which preparations contain substances which are sensitive to oxidation decomposition.

A further object is to obtain a possibility of packing pharmaceutical solutions in plastic packages also in those cases when the substances present are not so easily decomposed by oxidation, but where one hitherto has not managed to obtain storeability by means of plastic packages but only been restricted to glass ware packages.

Local anaesthetically active preparations containing adrenaline are examples of preparations which are very sensitive to oxidation, whereby the adrenaline is easily decomposed by oxidation.

Adrenaline is added to local anaesthetically active injection solutions in order to obtain a contraction of the vessels around the injection site and thereby to prevent the local anaesthetically active substance being removed too fast from the injection site. Adrenaline is thus added to reduce blood through-passage in the tissue to be anesthetized.

Adrenaline is very easily affected by oxygen from the environment and is thereby decomposited to non-active compounds.

In spite of the fact that the local anesthetically active solution containing adrenaline is stored in a cylinder ampoule of glass or plastic provided with a plunger of rubber in one end and a membrane of rubber in the other, relatively large amounts of air oxygen may pass through into the solution, the adrenaline present rapidly being oxidized. The amount of oxygen which passes into a cylinder ampoule of said type having a volume of 2 ml is not less than corresponding to 0.5 ml over a two-year period. As the amount of adrenaline is only 2.5–20 µg/ml it is understood that the adrenaline is very rapidly decomposited.

The demand is further great to be able to store for a long time such local anesthetic injection solutions and then also at temperatures which are within and above ambient temperature (+22° C.).

In present time it is needed to add additives to the injection solutions in order to prevent the oxidation of the adrenaline, whereby sodium pyrosulphite and preserving agents are added. There is thus a great request for completely or substantially completely eliminating such additives.

Besides adrenaline even noradrenaline and derivatives thereof may be present in local anesthetic preparations.

It has now become possible to prevent oxidation decomposition of oxidation sensitive substances in pharmaceutically active solutions stored in cylinder ampoules, disposable injection syringes, injection solution flasks, and such units by means of the present invention which is characterized in that one encloses one or more such units in an oxygen impervious outer package and that one then introduces hydrogen and a catalyst of the reaction of hydrogen and oxygen to water, in the same.

A preferred embodiment of the invention is characterized in that the volume of the hydrogen introduced is at least twice the volume of oxygen present in the outer package.

A further, preferred embodiment of the invention is characterized in that one introduces inert gas into the package prior to the introduction of hydrogen.

Another preferred embodiment of the invention is characterized in that one evacuates the packages, possibly after a preceding introduction of inert gas, prior to the introduction of hydrogen.

A preferred embodiment is characterized in that one introduces hydrogen in an amount of up to 8% of the free inner volume of the package.

Another preferred embodiment is characterized in that the catalyst is palladium, platinum, rhodium, osmium, iridium or ruthenium.

A further, preferred embodiment of the invention is characterized in that the pharmaceutically active solution contains a local anesthetically active compound and a compound of the group adrenaline, noradrenaline and derivatives of these.

Another object of the invention is a package for the protection of pharmaceutically active solutions containing oxidation decomposable substances, which solutions are stored in cylinder ampoules, disposable injection syringes, injection solution flasks, and such units, whereby the invention is characterized in an oxygen impervious outer package containing one or more of said units and an addition of hydrogen and a catalyst of the reaction of hydrogen and oxygen to water.

A preferred embodiment of the invention is characterized in that the outer package moreover contains an addition of inert gas.

Another preferred embodiment is characterized in that the outer package consists of a metallic container.

Another further, preferred embodiment is characterized in that the outer package consists of a laminate of aluminum foil-plastic foil, which laminate has been sealed via the plastic foil to the formation of a space receiving said units.

A further, preferred embodiment of the invention is characterized in that said units contain a local anesthetically active solution and a compound of the group of adrenaline, noradrenaline and derivatives of these.

An inert gas nitrogen gas and/or carbon dioxide may preferably be used, but quite obvious other protecting gases, as argon, may also be considered.

The amount of hydrogen gas has been said above to be up to 8% of the free, inner volume of the outer package. However, the molar amount of hydrogen gas shall in each case always be at least twice the residual molar amount of oxygen, i.e. that the volume of hydrogen gas shall be double the volume of oxygen gas in the package in order to obtain a guaranteed complete reaction of hydrogen-oxygen to water.

Local anesthetically active compounds of general occurrence, which are present as injection solutions with an addition of adrenaline is lidocaine (Xylocaine ®), bupivacaine (Marcaine ®), mepivacaine (Carbocaine ®), and prilocaine (Citanest ®). Also other compounds may occur together with adrenaline.

Suitable catalysts are the so called platinum metals platinum, palladium, rhodium, osmium, iridium, and ruthenium, which all catalyze the reaction hydrogen-oxygen to water. The catalyst which is only added in small amounts is preferably added together with a carrier such as carbon.

The catalyst may be added to the package in pulverulent form, in tablet form, or bound to a foil shaped carrier, whereby in the latter case the catalyst may be fastened to the inner side of the package, and whereby the foil shaped carrier may contain an indicator compound to indicate a possible presence of free oxygen. Methylene blue is such an indicator compound, which changes from blue to white in the absence of oxygen.

The outer package shall consist of an oxygen impervious casing, suitably a metallic casing, such as of sheet-iron or aluminum foil which has been laminated with a plastic foil so that the plastic foil serves as a sealing member when one produces an outer package. The plastic foils are thereby heat-sealed to each other, whereby different methods to increase the area of the sealing zone may be used such as rifling or "waffling" thereof.

The present invention will be described more in detail below in relation to the Figure 10 cylinder ampoules (1) made of glass and comprising a cylindrical body being somewhat tapered in one end and provided each in this end with a rubber membrane being piercable with an injection needle and in the other end with a rubber plunger which ampoules contain each 1.8 ml of an injection solution. The injection solution contains 20 mg of lidocaine hydrochloride per ml and adrenaline bitartrate corresponding to 12.5 $\mu$g of adrenaline per ml. The cylinder ampoules were packed in an outer casing (2) consisting of a laminate of aluminum foil—plastic foil. In the outer casing nitrogen gas—hydrogen gas mixture (92:8) is introduced and 0.1 mg of palladium in the form of 5% Pd on carbon (3). In spite of the nitrogen gas introduction there is, immediately after sealing of the package, in the package minor amounts of oxygen left. At a check-up 1 h after, no analyzable amounts of free oxygen are present in the package.

At forced storing tests free oxygen has not in any case been able to be analyzed and the amount of adrenaline has been constant, 12.5 $\mu$g, all the time.

By means of the present invention that further advantage can be achieved that the units containing the injection solution containing adrenaline such as cylinder ampoules, disposable injection syringes and flasks, so called vials not necessarily need to be made of glass but can be made of another material which is not oxygen impervious per se as glass is, provided that other criteria for the storage of the injection solutions are fullfilled.

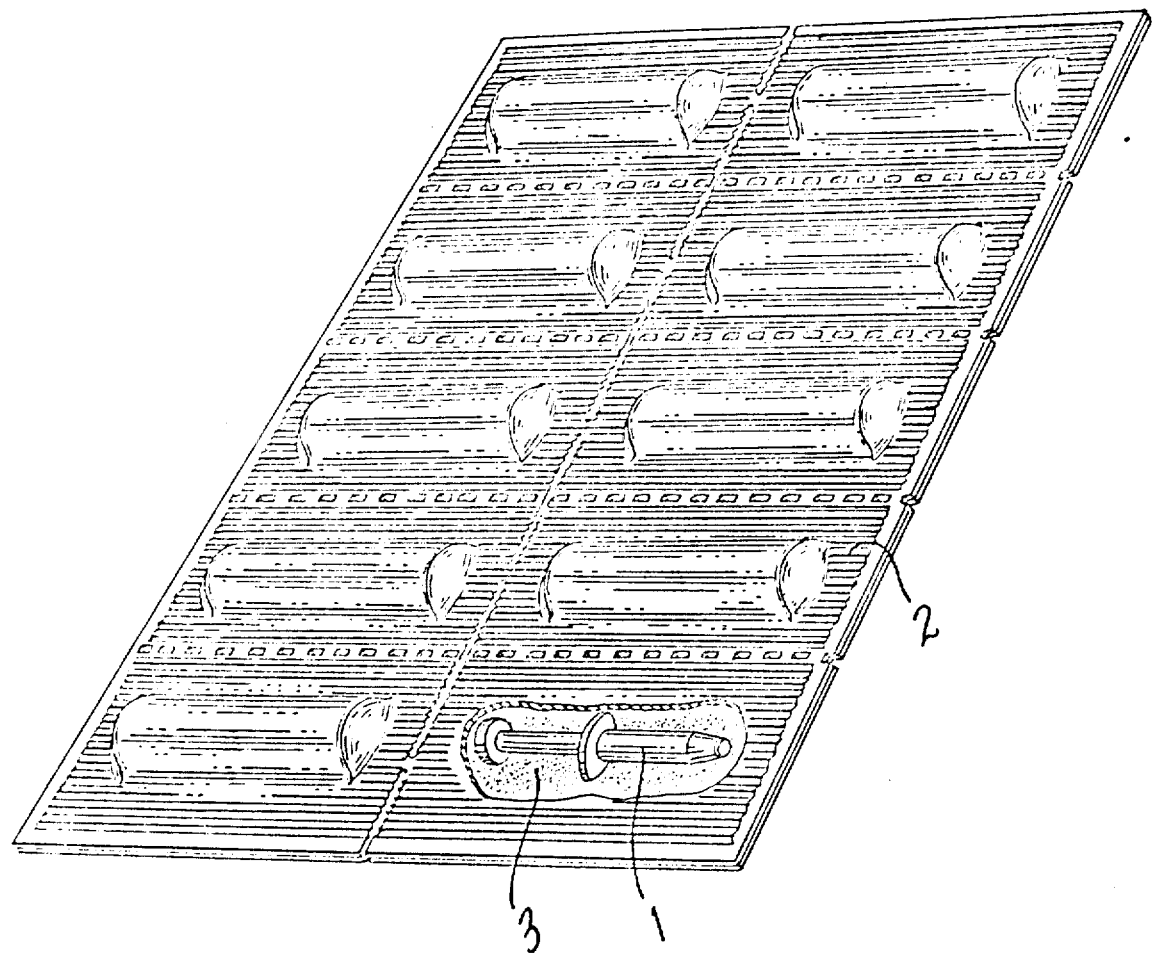

I claim:

1. Package for the protection of oxidizable compounds selected from the group consisting of adrenaline, noradrenaline and derivatives thereof which are present in pharmaceutically active solutions containing a local anesthetically active compound, which solutions are stored in a container which is further enclosed in an oxygen gas impervious outer package containing hydrogen gas and a catalyst which catalyzes the reaction of hydrogen and oxygen into water present in the space between said container and said outer package.

2. Package according to claim 1, characterized in that the volume of hydrogen gas is at least twice the volume of oxygen gas.

3. Package according to any of claims 1 or 2, characterized in that the outer package further comprises inert gas.

4. Package according to claim 1, characterized in that the outer package consists of a metal container.

5. Package according to claim 4, characterized in that the outer package consists of a laminate composed of aluminum foil-plastic foil, which laminate has been sealed via the plastic foil to the formation of a space receiving said units.

6. A method for preventing oxidation of a compound selected from the group consisting of adrenaline, noradrenaline, and derivatives thereof which are sensitive to oxidation and present in pharmaceutically active solutions containing a local anesthetically active compound and stored in a container wherein said container is further enclosed in an oxygen gas impervious outer package and hydrogen gas and a catalyst which catalyzes the reaction of hydrogen and oxygen to water are introduced into the space between said container and said outer package.

7. Process according to claim 6, characterized in that the volume of the hydrogen gas introduced is at least twice the volume of oxygen gas present in the outer package.

8. Process according to claim 6, characterized in that one introduces inert gas into the package prior to the introduction of hydrogen gas.

9. Process according to claim 6, characterized in that one evacuates the package prior to the introduction of hydrogen gas.

10. Process according to claims 6 or 4, characterized in that one carries out an introduction of inert gas prior to the evacuation and the introduction of hydrogen gas.

11. Process according to claim 6, characterized in that one introduces hydrogen gas in an amount that is up to 8% of the inner free volume of the package.

* * * * *

UNITED STATES PATENT AND TRADEMARK OFFICE
CERTIFICATE OF CORRECTION

PATENT NO. : 4,236,633

DATED : December 2, 1980

INVENTOR(S) : Lennart S. Ernerot

It is certified that error appears in the above—identified patent and that said Letters Patent is hereby corrected as shown below:

IN THE DRAWING:

Please add the drawing, as shown on the attached sheet:

On the Cover Page, "No Drawings" should read -- 1 Drawing Figure --.

On the cover page under "[56] References Cited" please add the following references:

4,057,047 11/19/77 Gossett 206/219
4,078,892 3/1978 Steinbrink 206/219
4,093,067 6/1978 Hollander 206/219

In Column 3, line 21 please add a period after the word "Figure."

In Column 4, line 45, "claims 6 or 4" should read --claims 6 or 9--.

Signed and Sealed this

Twenty-first Day of July 1981

[SEAL]

Attest:

GERALD J. MOSSINGHOFF

Attesting Officer     Commissioner of Patents and Trademarks

UNITED STATES PATENT AND TRADEMARK OFFICE
CERTIFICATE OF CORRECTION

PATENT NO. : 4,236,633
DATED : December 2, 1980
INVENTOR(S) : Lennart S. Ernerot It is certified that error appears in the above—identified patent and that said Letters Patent is hereby corrected as shown below: